(12) United States Patent
Suryanarayanan et al.

(10) Patent No.: US 7,953,262 B2
(45) Date of Patent: May 31, 2011

(54) VASCULAR IMAGE EXTRACTION AND LABELING SYSTEM AND METHOD

(75) Inventors: Srikanth Suryanarayanan, Karnataka (IN); Yogisha Mallya, Karnakata (IN); Krishna Seetharam Shriram, Karnataka (IN); Ajay Gopinath, Karnataka (IN); Mukta C. Joshi, Belmont, MA (US)

(73) Assignee: General Electric Company, Niskayuna, NY (US)

( * ) Notice: Subject to any disclaimer, the term of this patent is extended or adjusted under 35 U.S.C. 154(b) by 954 days.

(21) Appl. No.: 11/702,318

(22) Filed: Feb. 5, 2007

(65) Prior Publication Data
US 2008/0188962 A1    Aug. 7, 2008

(51) Int. Cl.
*G06K 9/00* (2006.01)
(52) U.S. Cl. .......................... 382/128; 382/131; 382/173
(58) Field of Classification Search .................. 382/128, 382/173
See application file for complete search history.

(56) References Cited

U.S. PATENT DOCUMENTS

| | | | |
|---|---|---|---|
| 7,177,453 B2 | 2/2007 | Suryanarayanan et al. | |
| 7,711,165 B2 * | 5/2010 | Lesage et al. | 382/128 |
| 2003/0031351 A1 | 2/2003 | Yim | |
| 2005/0110791 A1 * | 5/2005 | Krishnamoorthy et al. | 345/419 |
| 2005/0113679 A1 * | 5/2005 | Suryanarayanan et al. | 600/425 |
| 2006/0120585 A1 * | 6/2006 | Zhang et al. | 382/131 |
| 2008/0146951 A1 * | 6/2008 | Zhao et al. | 600/504 |

OTHER PUBLICATIONS

Netherlands Search Report.
Suryanarayanan et al., "Automatic Tracking of Neuro Vascular Tree Paths", Proc. of SPIE, vol. 6144, pp. 61444N-1 thru 61444N-8, XP-002550700.
Zhang et al., "Automatic Detection of Three-Dimensional Vascular Tree Centerlines and Bifurcations in High-Resolution Magnetic Resonance Angiography", Investigative Radiology, vol. 40, No. 10, Oct. 2005, pp. 661-671, XP-008113336.
Zhou et al., "Efficient Skeletonization of Volumetric Objects", IEEE Transactions on Visualization and Computer Graphics, vol. 5, No. 3, pp. 196-209, Jul.-Sep. 1999.

(Continued)

*Primary Examiner* — Tom Y Lu
(74) *Attorney, Agent, or Firm* — Scott J. Asmus (57) ABSTRACT

A technique for producing a three-dimensional segmented image of blood vessels and automatically labeling the blood vessels. A scanned image of the head is obtained and an algorithm is used to segment the blood vessel image data from the image data of other tissues in the image. An algorithm is used to partition the blood vessel image data into sub-volumes that are then used to designate the root ends and the endpoints of major arteries. An algorithm is used to identify a seed-point voxel in one of the blood vessels within one of the sub-volume of the partition. Other voxels are then coded based on their geodesic distance from the seed-point voxel. An algorithm is used to identify endpoints of the arteries. This algorithm may also be used in the other sub-volumes to locate the starting points and endpoints of other blood vessels. One sub-volume is further sub-divided into left and right, anterior, medial, and posterior zones. Based on their location in one of these zones, the voxels corresponding to the endpoints of the blood vessels are labeled. Starting from these endpoints, the artery segments are tracked back to their starting points using an algorithm that simultaneously labels all of the blood vessel voxels along the path with a corresponding anatomical label identifying the blood vessel to which it belongs.

31 Claims, 6 Drawing Sheets

OTHER PUBLICATIONS

Bulliet et al., "Reconstruction of the Intracerebral Vasculature from MRA and a Pair of Projection Views", , Medical Image Display and Analysis Group, University of North Carolina, Chapel Hill, Nc, 4 pages, Date: 1997.

Bullitt et al., "Computer-Assisted Measurement of Vessel Shape From 3T Magnetic Resonance Angiography of Mouse Brain", Methods, vol. 43, pp. 29-34, 2007.

Nowinski et al., The Cerefy Atlas of Cerebral Vasculature (1st edition), Date: 2009.

Kass et al., "Snakes: Active Contour Models", International Journal of Computer Vision, pp. 321-331, 1988.

Takemura et al., "Automatic Segmentation Method Which Divides a Cerebral Artery Tree in Time-Of-Flight MR-Angiography Into Artery Segments", Proc. of SPIE, vol. 6144, pp. 61443G-1 to 61443G-9, 2006.

Bullitt et al., "Measuring Tortuosity of the Intracerebral Vasculature From MRA Images", IEEE Transactions on Medical Imaging, vol. 22, No. 9, pp. 1163-1171, Sep. 2003.

Sato et al., "Three-Dimensional Multi-Scale Line Filter for Segmentation and Visualization of Curvilinear Structures in Medical Images", Medical Image Analysis, vol. 2, No. 2, pp. 143-168, 1998.

Villablanca et al., "Detection and Characterization of Very Small Cerebral Aneurysms By Using 2D and 3D Helical CT Angiography", AJNR Am J Neuroradiol, vol. 23, pp. 1187-1198, Aug. 2002.

Saha et al., "Automatic Bone-Free Rendering of Cerebral Aneurysms via 3D-CTA", Medical Imaging 2001: Image Processing, Proc. SPIE, vol. 4322, pp. 1264-1272, 2001.

Suryanarayanan et al., "Automatic Tracking of Neuro Vascular Tree Paths", Medical Imaging 2006: Image Processing, Proc. SPIE, vol. 6144, pp. 61444N-1 to 61444N-8, 2006.

* cited by examiner

VASCULAR IMAGE EXTRACTION AND LABELING SYSTEM AND METHOD

BACKGROUND

The invention relates generally to the field of medical imaging. More particularly, the present invention relates to a technique for automatically identifying and labeling blood vessels in a medical image.

Volumetric medical imaging systems have become a valuable tool in the diagnosis and treatment of many illnesses and diseases. As opposed to conventional X-ray imaging systems that are only able to gather only two-dimensional information about a patient's internal anatomical features, volumetric medical imaging systems are able to gather internal anatomical information in three-dimensions. This three-dimensional information can then be used to form medical images from a variety of different perspectives, whereas conventional X-ray images are limited to an image from a single view. Examples of volumetric imaging systems are Computed Tomography (CT) imaging systems, Magnetic Resonance Imaging (MRI) systems, and Positron Emission Tomography (PET).

One factor that can impair the usefulness of these imaging technologies is the relative difficulty in discerning a particular structure of interest from its background, especially when the background has a similar texture or structure. Segmentation programs have been developed to facilitate the examination of specific anatomical features by eliminating non-desired anatomical features from the image. For example, segmentation programs have been developed that enable bone to be removed from an image so that soft tissues may be observed more easily. In some applications, problems in identifying an anatomical feature may still exist after segmentation. For example, a segmentation program may be used to segment the blood vessels within the skull that supply the brain from other soft tissues and bone. However, the large number of blood vessels remaining after segmentation makes identifying a specific blood vessel difficult. In addition, the blood vessels of the brain make many twists and turns, as well as intertwine, making it even more difficult to identify a specific blood vessel. As a result, it may be difficult to identify or track an individual blood vessel as it courses its way around the brain.

Images of the blood vessels of the brain are of great interest to radiologists. For example, a radiologist will be interested in identifying the blood vessel segment that is occluded if the purpose of a scan is for the detection of an ischemic stroke. On the other hand, if the purpose of the scan is the detection of a hemorrhagic stroke, a radiologist will be interested in locating vessel junctions (or bifurcation points), which are a common location of aneurysms. However, a normal segmented image of the blood vessels of the brain may not be particularly helpful in either situation. It may be difficult for the radiologist to identify the specific blood vessel involved. Furthermore, it may be difficult to distinguish a bifurcation point in a blood vessel from simply the overlapping of two blood vessels.

Therefore, a need exists for a technique that will overcome the problems described above. The techniques described below may solve one or more of these problems.

BRIEF DESCRIPTION

A technique for producing a three-dimensional segmented image of blood vessels within a patient's skull and to automatically label the blood vessels is provided. However, the technique is applicable to blood vessels in other portions of the body, as well. An image of the head is obtained and an algorithm is then used to segment the blood vessel image data from the image data of other tissues in the image to form what is known as a "vessel tree." An algorithm is used to partition the head, and thus the blood vessel image data, into sub-volumes that are then used to designate the root ends and the endpoints of the major arteries within the vessel tree. An algorithm is used to identify a voxel in one of the internal carotid arteries located within the lower sub-volume of the partition. The voxels in the rest of the vessel tree are then coded based on their geodesic distance from the voxel in the internal carotid artery. In the upper sub-volume, local distance maxima are used to identify endpoints of the arteries in the vessel tree. This algorithm may also be used in the other sub-volumes to locate the starting points and endpoints of other blood vessels. The upper sub-volume is further subdivided into left and right anterior, medial, and posterior zones. Based on their location in one of these zones, the voxels corresponding to the endpoints of the blood vessels are labeled. Starting from these terminal points, the artery segments are tracked back using a shortest path algorithm that simultaneously labels all of the blood vessel voxels along the path with a corresponding anatomical label identifying the blood vessel to which it belongs. Multiple tracks that meet are tagged and labeled as bifurcation points.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
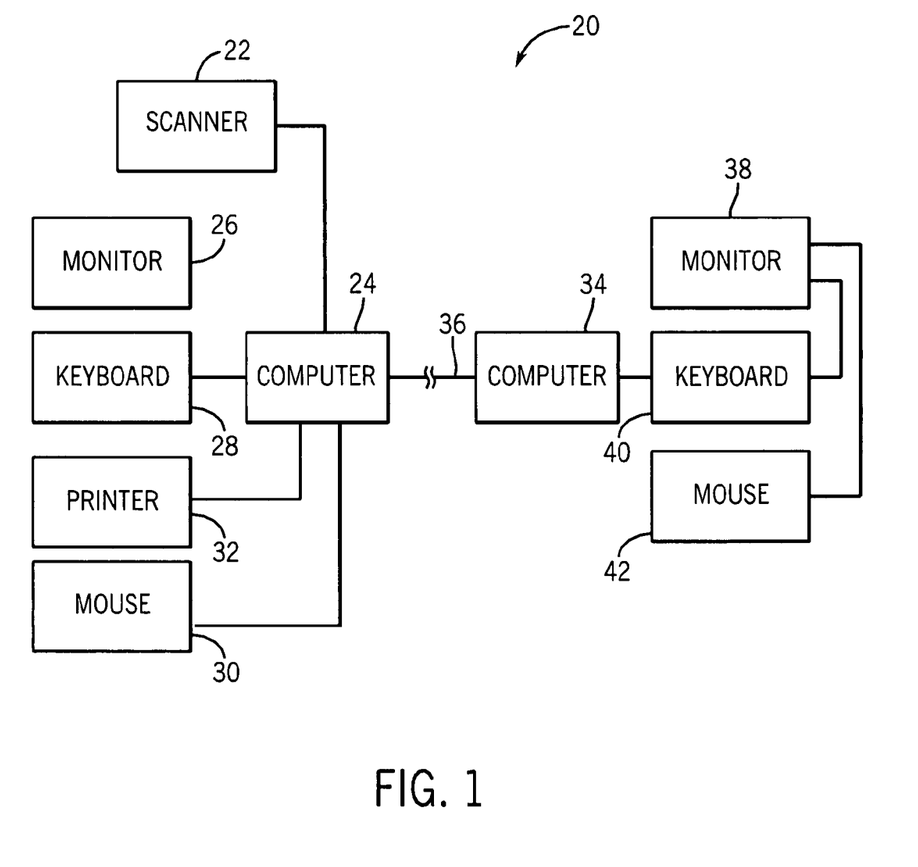
FIG. 1 is a block diagram of a medical imaging system, in accordance with an exemplary embodiment of the present technique.

Referring generally to FIG. 1, a diagrammatical view of a medical imaging system 20 having a scanner 22 that is operable to scan a patient in three-dimensions and to produce medical image data of the internal anatomy of a patient is provided. The scanner 22 may utilize any of a variety of different imaging modalities, such as Computed Tomography (CT), Magnetic Resonance (MR), or Positron Emission Tomography (PET). In this embodiment, the medical image data obtained by the scanner 22 is in a digital form. Three-dimensional images are comprised of voxels. A voxel in three-dimensional medical imaging is analogous to a pixel in two-dimensional imaging. A voxel is a volume element represents a value in a grid in three-dimensional space. The scanner 22 is operable to assign values to the voxels. The value of a voxel may represent various properties. In CT scans, the values are Hounsfeld units that represent the opacity of material to X-rays. In MR imaging, the voxels represent a different property.

The scanner 22 is connected to a local computer 24 that enables a user to operate the scanner 22 and other components of the medical imaging system 20. The local computer 24 is operable to receive the medical image data produced by the scanner 22 and to process the medical image data to produce a medical image of the patient. A monitor 26, a keyboard 28, and a mouse 30 are provided to enable a user to interact with the local computer 24. A user may use these devices to instruct the local computer 24 to direct the scanner 22 to scan desired portions of a patient. In addition, a printer 32 is provided to enable hard copies of medical images to be printed.

A radiologist may receive and manipulate medical images using a remote computer 34 that is connected to the local computer 24 via a communications network 36, such as the Internet or as part of a PACS. Medical image data from the scanner 22 may be retrieved by the remote computer 34 for diagnostic purposes or for further processing. As with the local computer 24, the remote computer 34 is provided with a monitor 38, a keyboard 40, and a mouse 42 to enable a user to interact with the remote computer 34.

In the illustrated embodiment, the remote computer 34 is provided with programming that enables it to process the medical image data to produce a three-dimensional segmented image of blood vessels and to automatically label individual blood vessels, as well as identifying the path of these individual blood vessels, including the starting and ending points. As a result, the program enables a user to follow the path of an individual blood vessel as it twists and turns and intertwines with other blood vessels. In addition, the programming also directs the remote computer 34 to automatically identify blood vessel bifurcation points. Furthermore, the program enables a user to direct the remote computer 34 to remove undesired blood vessels from the medical image, such as those blood vessels not on a path of interest. Alternatively, the programming may be stored within the local computer 24, rather than the remote computer 34, or they may both have the programming. In this embodiment, the medical imaging system 20 is being utilized to produce a three-dimensional segmented image of anatomically-labeled blood vessels within the skull that supply blood to the brain. However, the medical imaging system 20 may be used to provide images of other blood vessels, such as the blood vessels of the heart.

Figure 2:
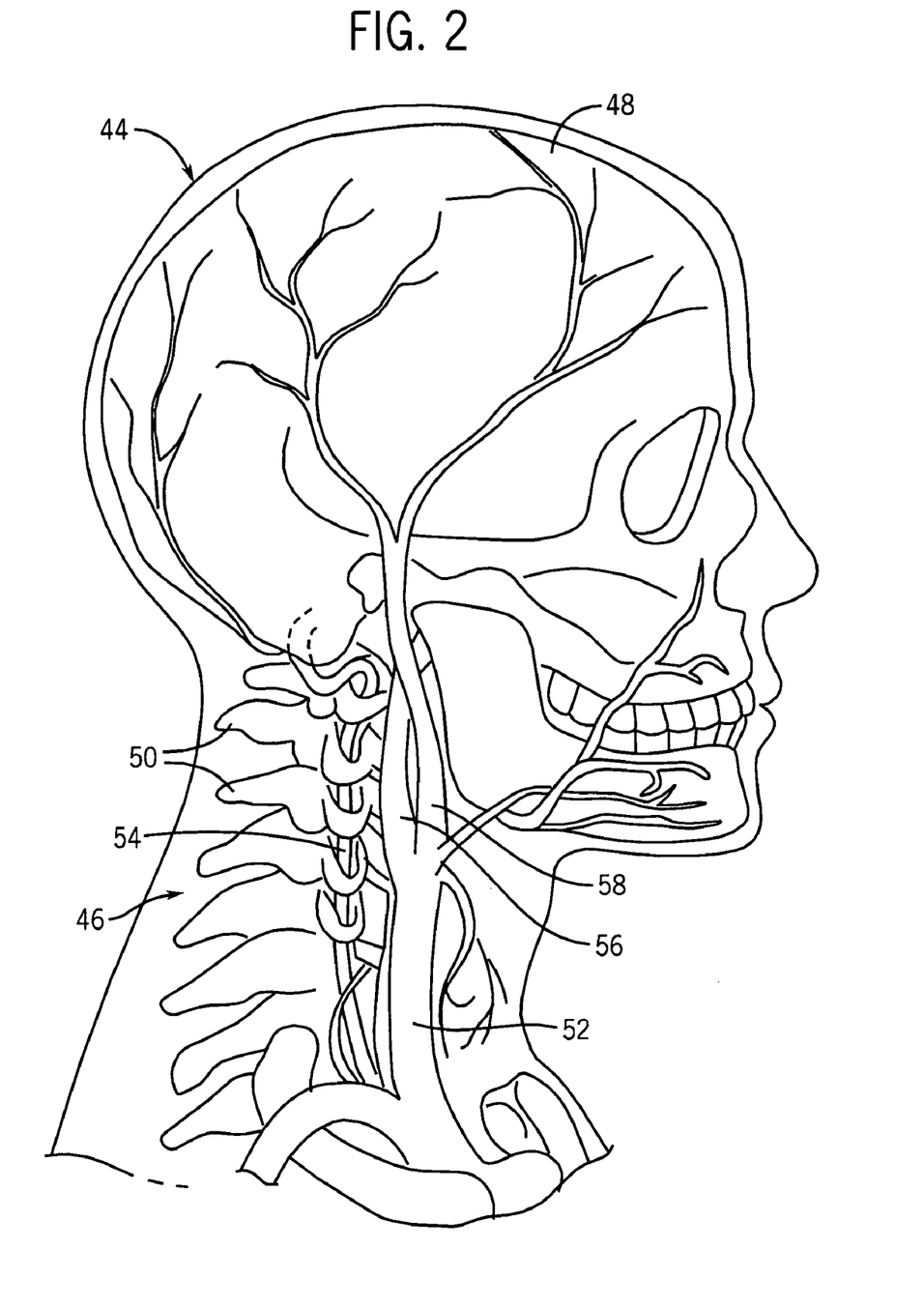
FIG. 2 is an anatomical drawing of some of the internal anatomical features of the head and neck.

Referring generally to FIG. 2, a view of the right side of a patient's head 44 and neck 46 are provided. The brain is housed in the cranial cavity inside a patient's skull 48, which is supported by cervical vertebra 50 in the neck 46. The head 44 receives blood from the right common carotid artery 52, the left common carotid artery (not shown in this view), the right vertebral artery 54, and the left vertebral artery (also not shown in this view). The left common carotid artery and the left vertebral artery are located on the opposite side of the head 44. The right common carotid artery 52 splits into a right internal carotid artery 56 and a right external carotid artery 58. Similarly, the left common carotid artery also splits into a left internal carotid artery and a left external carotid artery. The right vertebral artery 54 and left vertebral artery extend through the cervical vertebra 50 and up into the skull 48 through the foramen magnum to supply blood to the brain. The right internal carotid artery 56 and the left internal carotid artery pass through the foramen lacerum into the skull 48. The right and left external carotid arteries supply blood to blood vessels of the head 44 outside of the skull 48, such as the facial muscles.

Figure 3:
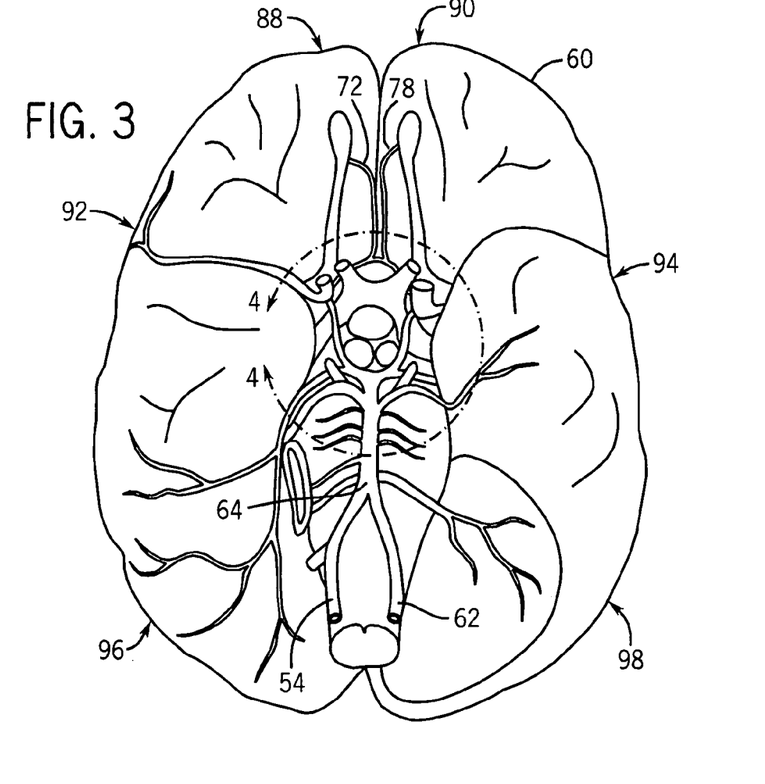
FIG. 3 is a bottom view of a portion of the brain, illustrating the major arteries of the brain.
Figure 4:
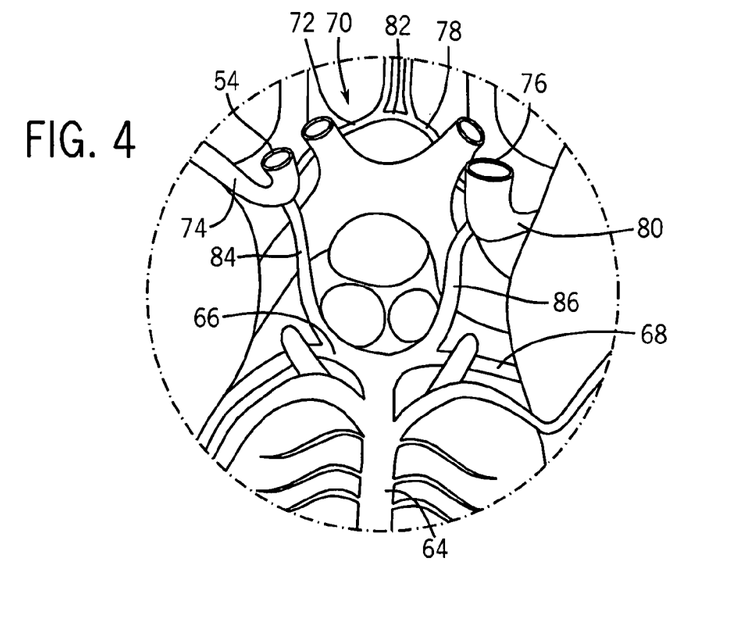
FIG. 4 is an expanded view of a portion of FIG. 4, illustrating the Circle of Willis.

Referring generally to FIGS. 3 and 4, the arteries supplying blood to the brain merge to form a network of blood vessels inside the skull 48 that supply blood to the various portions of the brain 60. Toward the posterior end of the brain 60, the right vertebral artery 54 and the left vertebral artery 62 merge to form the basilar artery 64. The basilar artery 64 passes along the ventral brainstem and has branches that supply blood to the pons, the midbrain, and the cerebellum. The basilar artery 64 terminates by dividing into a right posterior cerebral artery 66 and a left posterior cerebral artery 68 that supply portions of the occipital and temporal lobes of the cerebrum.

As best illustrated in FIG. 4, the posterior cerebral arteries also form a portion of the cerebral arterial circle, also known as the Circle of Willis, referenced generally by reference numeral 70, at the base of the brain 60. The Circle of Willis 70 is a circle of arteries that connect the vertebral arterial system and the carotid arterial systems and provides alternate pathways through which blood can reach the tissues of the brain in the event that a blood vessel becomes blocked or narrows. The internal carotid arteries also form part of the Circle of Willis 70. The right internal carotid artery 56 terminates by branching into a right anterior cerebral artery 72 and a right middle cerebral artery 74. Similarly, the left internal carotid artery 76 terminates by branching into a left anterior cerebral artery 78 and a left middle cerebral artery 80. The right anterior cerebral artery 72 is joined to the left anterior cerebral artery 78 by the anterior communicating artery 82. The right middle cerebral artery 74 is connected to the right posterior cerebral artery 66 by the right posterior communicating artery 84. Similarly, the left middle cerebral artery 80 is connected to the left posterior cerebral artery 68 by the left posterior communicating artery 86, completing the Circle of Willis 70.

Referring again to FIG. 3, the cerebral arteries extend around the brain 60 and branch into many smaller arteries that supply blood to the brain 60. The names of the various cerebral arteries suggest their ultimate destinations. The right anterior cerebral artery 72 supplies blood to the right anterior portion 88 of the brain 60. The left anterior cerebral artery 78 supplies blood to the left anterior portion 90 of the brain 60. The right middle cerebral artery 74 supplies blood to the right middle portion 92 of the brain 60. The left middle cerebral artery 80 supplies blood to the left middle portion 94 of the brain 60. The right posterior cerebral artery 66 supplies blood to the right posterior portion 96 of the brain 60. Finally, the left posterior cerebral artery 68 supplies blood to the left posterior portion 98 of the brain 60.

Figure 5:
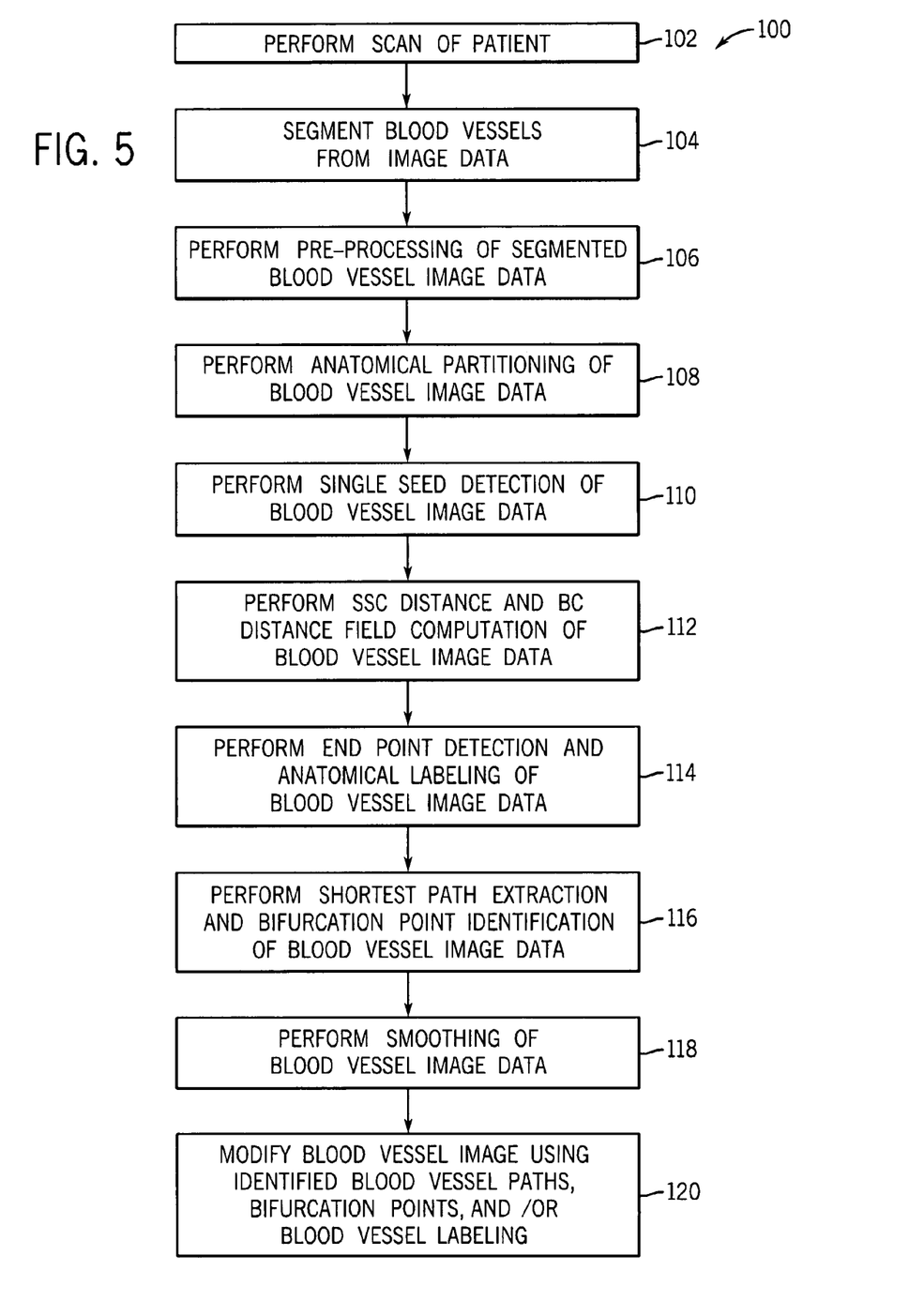
FIG. 5 is a block diagram of a method of producing a segmented image of blood vessels of the brain with the identity of the blood vessels established automatically, in accordance with an exemplary embodiment of the present technique.

Referring generally to FIG. 5, a block diagram of a technique for producing a three-dimensional segmented image of blood vessels within a patient's skull and to automatically label the blood vessels is provided, and referenced generally by reference number 100. As will be discussed in more detail below, an image of the head is obtained and an algorithm is then used to segment the blood vessel voxels from the voxels corresponding to other tissues in the image, so as to form a vessel tree. An algorithm is also used to partition the head into three sub-volumes that are then used to designate the root ends and the endpoints of the major arteries of the vessel tree. An algorithm is then used to identify a voxel in the internal carotid arteries located within the lower sub-volume of the head partition. The voxels in the rest of the vessel tree are then coded based on their geodesic distance from the voxel in the internal carotid artery. In the upper sub-volume, local distance maxima are used to identify endpoints of the arteries in the vessel tree. The upper sub-volume is further sub-divided into left and right anterior, medial, and posterior zones. The voxels corresponding to the endpoints are labeled based on their location in one of these zones. Starting from these endpoints, the artery segments are tracked back using a shortest-path algorithm that simultaneously labels all of the blood vessel voxels along the path with a corresponding anatomical label. Multiple tracks that meet are tagged and labeled as bifurcation points. Please note that this technique may be used for blood vessels in other parts of the body, as well.

The first block of the technique, referenced generally by block 102, is to perform a scan of the patient's head using the scanner 22 of the medical imaging system 20 of FIG. 1. When performing a scan of the patient's head, data from anatomical features other than blood vessels will be present, such as bone image data, brain matter image data, nerve image data, etc. Typically, a contrasting agent is injected into the patient's bloodstream that will enhance the difference between blood vessels and other anatomical features. For example, image data may be obtained from CT angiography, Time-of-Flight (TOF) MR angiography, contrast enhanced MR Angiography, or a similar procedure. The medical imaging data obtained from the scan of the patient's head may be stored for review by a radiologist or for further processing. So far, the technique has involved standard medical image production techniques. Further processing of the medical imaging data may be performed by a radiologist or someone else.

In this embodiment, further processing of the medical image data begins with a segmentation algorithm, represented generally by block 104. The segmentation algorithm is operable to identify voxels that correspond to blood vessels from voxels that correspond to other tissues. The blood vessels segmented from the other tissues form the vessel tree. Please note that this block and some or all of the following blocks may be performed automatically once initiated.

Segmented blood vessel image data is then processed using a pre-processing algorithm, represented generally by block 106. Depending on the angiography procedure performed, such as CT angiography or TOF MR angiography, contrast enhanced MR angiography, the segmented medical image data is cleaned up by an algorithm that is operable to remove stray structures. For example, a bone removal algorithm may be used to clean the image data from CT angiography, whereas an intensity and volume constraint-based approach may be used with TOF MR angiography. The segmentation algorithm may identify the features of interest by reference to known or anticipated image characteristics, such as edges, identifiable structures, boundaries, changes or transitions in colors or intensities, changes or transitions in spectrographic information, and so forth. In the illustrated embodiment, the segmented volume is cleaned and labeled using three-dimensional connected components with a threshold size of 1500 mm³. This volume threshold is used to remove the small external carotid arteries and veins. However, the major arterial blood vessel segments remain, such as the carotid arteries and the vertebral arteries.

After pre-processing, the blood vessel image data is processed with a head partition algorithm, represented generally by block 108. In this embodiment, the head partition algorithm partitions the head and neck into three sub-volumes. These sub-volumes include an inferior partition (IP) in which the arteries are circular in cross-section, but touch or pass through the bone, a middle partition (MP) in which the vessels loop through the Circle of Willis, and a superior partition (SP) in which the vessels branch to the different regions of the brain.

The image data that is partitioned into three head partitions is then processed automatically with a single-seed detection algorithm, as represented by block 110. A single-seed point refers to a "seed" voxel or set of voxels from which distances are referenced. The single-seed point algorithm is used in the inferior partition to identify a voxel in the internal carotid arteries to act as the single-seed point (i.e., starting point). In addition, the algorithm identifies the endpoints of blood vessels in the inferior partition.

A geodesic distance and boundary code computation algorithm is then executed through all three partitions, as referenced generally by block 112. All voxels on the vessel tree are referenced by their geodesic distance from the single-seed point. In the mathematical subfield of graph theory, the distance between two vertices in a graph is the number of edges in a shortest path connecting them. This is also known as the geodesic distance. A single-seed code is generated inside the vessel tree to establish the length of the shortest geodesic path between a voxel and the single-seed point. The single-seeded code classifies the object into a collection of clusters, where each cluster is the intersection between the blood vessel and a sphere, known as Viviani's curve, centered at a reference point within the blood vessel. Viviani's curve, also known as Viviani's window, is a space curve generated by four windows on a hemispherical dome so that the dome is rectifiable. The boundary code is the minimum distance to the boundary and is computed using a three-dimensional city block distance method.

An algorithm is also used to detect endpoints in the superior partition, as referenced generally by block 114. As noted above, the superior partition corresponds to the cranial region of the brain. The sub-volume is further divided into left and right regions for the middle cerebral artery and into a mid region for the anterior and posterior cerebral artery. By limiting the endpoint detection search only to these regions, false positives from veins and other structures are reduced. Local maximums in the single-seed code in the left, right, and the mid regions are identified as candidate endpoints. Based on their location in one of these zones, the voxels corresponding to the endpoints are labeled. For example, a voxel corresponding to an endpoint detected in the right anterior portion of the brain could be labeled "RACA" for right anterior cerebral artery.

Starting from these endpoints, the artery segments are tracked back from the superior partition to the inferior partition using a shortest path algorithm that simultaneously labels all of the blood vessel segment voxels along the path with a corresponding anatomical label, as referenced generally by block 116. The shortest path algorithm connects the endpoints with the starting point using a standard twenty-six neighbor region growing queue. Paths having a length greater than a threshold are considered valid branches to overcome spurious branches that can arise from segmentation artifacts or false "bridging". A bifurcation point is detected when the region growing encounters a previously tagged location, which implies that a path computed from another endpoint has already visited the location. The shortest-paths may be indicated on the medical image by a spline, color-coding the blood vessel segments, or some other visual indicator.

An active contour algorithm is then used in the illustrated algorithm to smooth the spline extracted by the shortest-path algorithm, as represented by block 118. Constraints are placed to ensure the spline does not cross over the vessel wall, particularly for small torturous vessels.

The blood vessel image may then be modified by the user based on the identified blood vessel paths, bifurcation points, and/or labeling, as represented by block 120. For example, blood vessel segments that are not needed may be removed from the medical image by the user.

Figure 6:
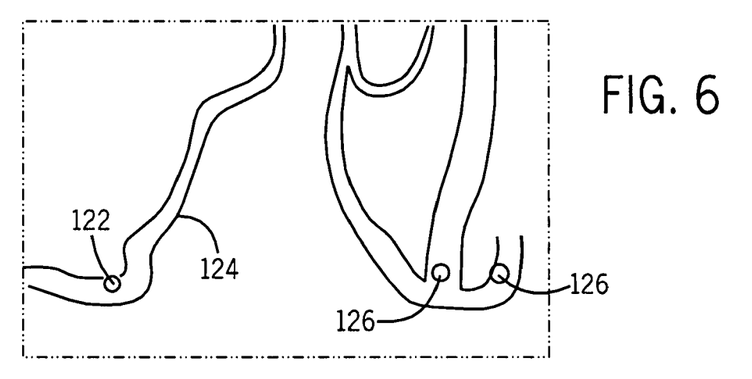
FIG. 6 is an embodiment of a medical image of a portion of the inferior partition of the brain, in accordance with an exemplary embodiment of the present technique.

Referring generally to FIG. 6, a portion of the image of the vessel tree in the inferior partition of the brain is provided. In the illustrated embodiment, the single-seed point 122 located on one of the internal carotid arteries 124 has been identified. In addition, endpoints 126 of arteries in the inferior partition have also been identified.

Figure 7:
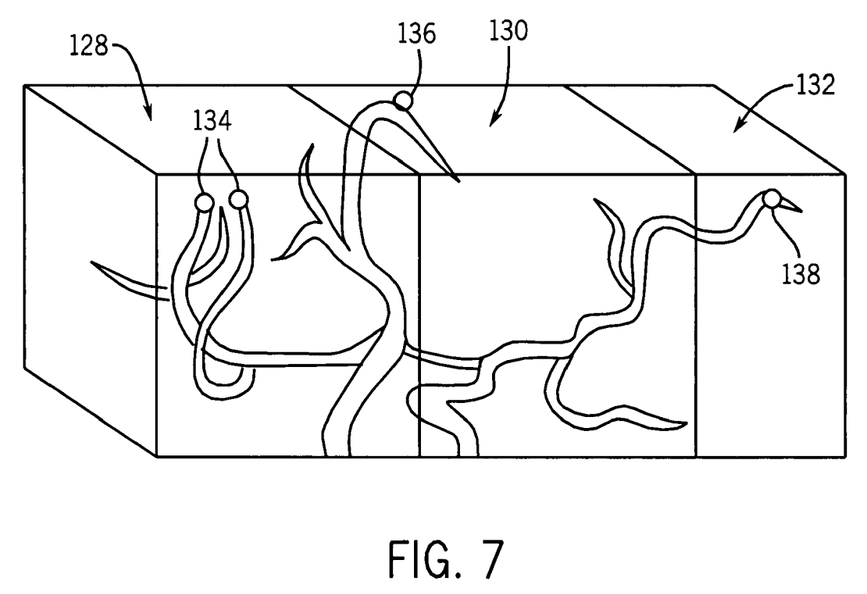
FIG. 7 is a representation of the superior partition of the brain being sub-divided into three regions and the detection of endpoints in blood vessels in all three regions, in accordance with an exemplary embodiment of the present technique.

Referring generally to FIG. 7, a view of one side of the superior partition of the brain is provided. As noted above, the superior partition is divided into a posterior region 128, a middle region 130, and an anterior region 132. The endpoints 134 located in the posterior region 128 are given an anatomical label to identify them as a blood vessel segment of a posterior cerebral artery. Similarly, the endpoints 136 located in the middle region 130 are given an anatomical label to identify them as a blood vessel segment of a middle cerebral artery. Finally, the endpoints 138 located in the anterior region 132 are given an anatomical label to identify them as a blood vessel segment of an anterior cerebral artery. These labels are maintained as the shortest-path algorithm tracks the blood vessel segments back to the single-seed point.

Figure 8:
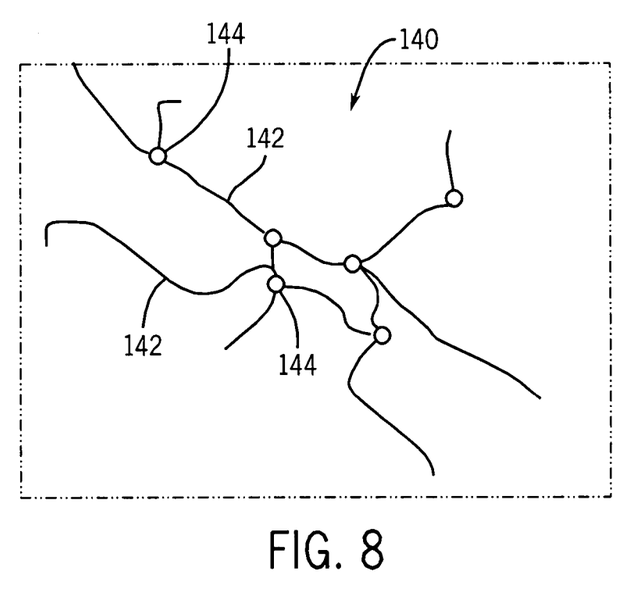
FIG. 8 is a representation of the spline formed by marking the paths of the blood vessel segments, in accordance with an exemplary embodiment of the present technique.

Referring generally to FIG. 8, an example of a spline of the paths of blood vessel segments is provided, referenced generally by reference numeral 140. The centerline paths of blood vessels segments are represented by lines 142. Bifurcation points are represented by circles 144 in this embodiment.

Figure 9:
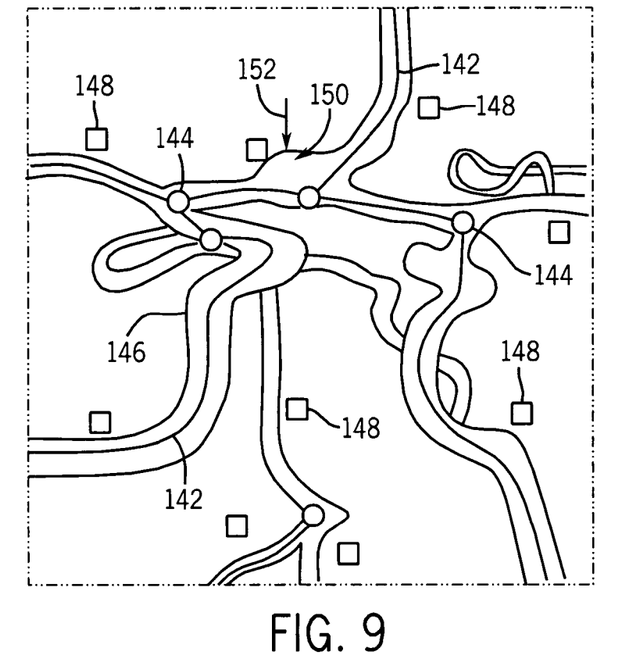
FIG. 9 is a segmented medical image of blood vessels having the paths of the blood vessel segments marked by a spline and labeled, in accordance with an exemplary embodiment of the present technique.

Referring generally to FIG. 9, a medical image of blood vessel segments produced in accordance with the above-described technique is provided. In addition to providing the image of the blood vessel segments 146, the lines 142 marking the centerline paths of the blood vessel segments 146 are overlaid onto the blood vessel segments 146. The circles 144 identifying the bifurcation points of blood vessel segments 146 are also provided. In this example, the identity of the blood vessel segments 146 is indicated by visual labeling 148. The visual labeling 148 may take many forms. The names may be spelled on the image next to the blood vessel segment 146 or a key may be used. In addition to or alternatively, the blood vessel segments 146 may be color-coded with different colors corresponding to different blood vessel segments 146. In this example, an aneurysm 150 is present. Note that the aneurysm 150 is located proximate to a bifurcation point. Here, the presence of the aneurysm 150 has been highlighted by placement of a reference arrow 152 adjacent to the aneurysm.

As a result of this technique, a user may quickly identify trouble spots within the blood vessels of the brain that have been identified automatically by the medical imaging system 20. For example, an aneurysm may be identified quickly and then marked on the image. The names of the blood vessels are identified automatically and labeled for easy retrieval. In addition, bifurcation points are identified automatically and marked on the medical image. All of these features, and others, may greatly facilitate the treatment and diagnosis of strokes and other vascular diseases.

Additional modification to the image may be performed. For example, blood vessel segments 146 may be color-coded. Blood vessel segments 146 may be deleted by a user using the lines 142 marking the centerline paths of the blood vessel segments 146 as a guide.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method of processing medical image data, comprising:
   partitioning image data representative of a plurality of blood vessels into a plurality of sub-volumes, wherein each sub-volume includes image data representative of blood vessels and the sub-volumes are defined by the physiological characteristics of the vessels within the respective sub-volumes;
   identifying a first voxel corresponding to a relative endpoint of a blood vessel;
   identifying the blood vessel corresponding to the first voxel based on the sub-volume in which the first voxel is located; and
   labeling the first voxel with data to identify the first voxel as being part of the blood vessel.

2. The computer-implemented method as recited in claim 1, comprising:
   identifying a second voxel corresponding to a relative starting point within the plurality of blood vessels; and
   labeling the second voxel with data to identify the second voxel.

3. The computer-implemented method as recited in claim 1, comprising:
   segmenting the image data representative of the plurality of blood vessels from image data representative of a patient's internal anatomy comprising the image data representative of the plurality of blood vessels.

4. The computer-implemented method as recited in claim 2, comprising:
   identifying a third voxel belonging to a specific blood vessel from among the image data representative of a plurality of blood vessels;
   establishing a relative distance of each voxel in the image data representative of the plurality of blood vessels to the third voxel;
   labeling each voxel with its relative distance to the third voxel; and
   tracking a path through the image data representative of the plurality of blood vessels from the first voxel corresponding to the relative endpoint to the second voxel corresponding to the relative starting point based on each voxels relative distance to the third voxel, wherein the algorithm labels each voxel along the path with data to identify the blood vessel corresponding to the relative endpoint of the blood vessel.

5. The computer-implemented method as recited in claim 4, wherein identifying the first voxel corresponding to the relative endpoint of the blood vessel is based on identifying a voxel having a local maximum in relative distance to the third voxel.

6. The computer-implemented method as recited in claim 4, wherein establishing the relative distance of each voxel in the image data representative of the plurality of blood vessels to the third voxel comprises establishing the geodesic distance of each voxel in the image data representative of the plurality of blood vessels relative to the third voxel.

7. The computer-implemented method as recited in claim 6, wherein tracking the path through the image data representative of the plurality of blood vessels comprises utilizing the geodesic distance of voxels in the image data representative of the plurality of blood vessels relative to the third voxel to establish the shortest path from the first voxel corresponding to the relative endpoint of the blood vessel to the second voxel corresponding to the relative starting point of the blood vessel.

8. The computer-implemented method as recited in claim 7, comprising:
   labeling a portion of the blood vessel as a bifurcation point when a first path tracked through the plurality of blood vessels merges with a second path tracked through the plurality of blood vessels that already has a voxel labeled with data to identify the blood vessel corresponding to the relative endpoint of the blood vessel.

9. The computer-implemented method as recited in claim 8, wherein labeling the portion of the blood vessel as the bifurcation point comprises identifying the specific bifurcation point.

10. The computer-implemented method as recited in claim 4, wherein identifying the third voxel from among the image data representative of the plurality of blood vessels is limited to a sub-volume corresponding to an expected location of the blood vessel.

11. The computer-implemented method as recited in claim 1, wherein identifying the first voxel corresponding to the relative endpoint of the blood vessel is limited to one or more sub-volumes corresponding to expected locations of endpoints of blood vessels.

12. The computer-implemented method as recited in claim 1, wherein partitioning the image data representative of the plurality of blood vessels into the plurality of sub-volumes comprises further partitioning a sub-volume into a left anterior zone, a left medial zone, a left posterior zone, a right anterior zone, a right medial zone, and a right posterior zone corresponding respectively to a left anterior cerebral artery, a left middle cerebral artery, a left posterior cerebral artery, a right anterior cerebral artery, and a right posterior cerebral artery.

13. The computer-implemented method as recited in claim 12, wherein identifying the blood vessel corresponding to the relative endpoint of the blood vessel based on the location of the relative endpoint of the blood vessel, comprises identifying the blood vessel by identifying the zone in which the relative endpoint of the blood vessel is located.

14. A computer-implemented method of processing medical image data, comprising:
   partitioning image data representative of a plurality of blood vessels into a plurality of sub-volumes that each include image data representative of the blood vessels, wherein the sub-volumes are defined by the physiological characteristics of the vessels within the respective sub-volumes;
   identifying a relative endpoint of a blood vessel of the plurality of blood vessels, wherein the blood vessel is identified based on the location of the relative endpoint;
   labeling a first voxel with data to identify the first voxel as corresponding to the relative endpoint of the blood vessel;
   tracking a path through image data representative of a plurality of blood vessels from the relative endpoint of the blood vessel toward a relative starting point of the blood vessel; and
   labeling each voxel along the path as corresponding to the blood vessel.

15. The computer-implemented method as recited in claim 14, comprising:
   segmenting the image data representative of the plurality of blood vessels from image data representative of a patient's internal anatomy comprising the image data representative of the plurality of blood vessels.

16. The computer-implemented method as recited in claim 14, wherein the location of the relative endpoint of the blood vessel is established from the sub-volume in which the relative endpoint of the blood vessel is located.

17. The computer-implemented method as recited in claim 16, wherein partitioning the image data representative of the plurality of blood vessels into the plurality of sub-volumes comprises partitioning a sub-volume into a left anterior zone, a left medial zone, a left posterior zone, a right anterior zone, a right medial zone, and a right posterior zone corresponding respectively to a left anterior cerebral artery, a left middle cerebral artery, a left posterior cerebral artery, a right anterior cerebral artery, and a right posterior cerebral artery.

18. The computer-implemented method as recited in claim 14, comprising:
   identifying a second voxel from among the image data representative of the plurality of blood vessels; and
   establishing a geodesic distance of each voxel in the image data representative of the plurality of blood vessels relative to the second voxel and labeling each voxel with its geodesic distance relative to the second voxel.

19. The computer-implemented method as recited in claim 18, wherein identifying the first voxel corresponding to the relative endpoint of the blood vessel is based on identifying a voxel having a local maximum in geodesic distance to the second voxel.

20. The computer-implemented method as recited in claim 19, wherein tracking the path through the image data representative of the plurality of blood vessels comprises utilizing the geodesic distance of voxels in the image data representative of the plurality of blood vessels relative to the second voxel to establish the shortest path from the first voxel corresponding to the relative endpoint of the blood vessel to the second voxel corresponding to the relative starting point.

21. The computer-implemented method as recited in claim 14, comprising:
   labeling a portion of the blood vessel as a bifurcation point when a first path tracked through the plurality of blood vessels merges with a second path tracked through the plurality of blood vessels that already has a voxel labeled with data to identify the blood vessel corresponding to the relative endpoint of the blood vessel.

22. The computer-implemented method as recited in claim 21, wherein labeling the portion of the blood vessel as the bifurcation point comprises labeling the bifurcation point as a specific bifurcation point.

23. A computer-implemented method of processing medical image data, comprising:
   partitioning image data representative of a plurality of blood vessels into a plurality of sub-volumes that each include image data representative of the blood vessels, wherein the sub-volumes are defined by the physiological characteristics of the vessels within the respective sub-volumes;
   identifying a relative endpoint of a blood vessel within a sub-volume of the plurality of sub-volumes;
   tracking a path through image data representative of a plurality of blood vessels from the relative endpoint of the blood vessel back toward a relative starting point of the blood vessel; and labeling a bifurcation point when a first path tracked through the plurality of blood vessels merges with a second path tracked through the plurality of blood vessels.

24. The computer-implemented method as recited in claim 23, comprising:
labeling each voxel along the path with data representative of the blood vessel corresponding to the relative endpoint of the blood vessel.

25. The computer-implemented method as recited in claim 23, wherein labeling the bifurcation point comprises labeling the bifurcation point as a specific bifurcation point.

26. A non-transitory machine-readable medium for processing medical image data, comprising:
code operable for partitioning image data representative of a plurality of blood vessels into a plurality of sub-volumes, wherein each sub-volume includes image data representative of blood vessels and the sub-volumes are defined by the physiological characteristics of the vessels within the respective sub-volumes;
code operable for identifying a first voxel corresponding to a relative endpoint of a blood vessel;
code operable for identifying the blood vessel corresponding to the first voxel based on the sub-volume in which the first voxel is located; and
code operable for labeling the first voxel with data to identify the first voxel as being part of the blood vessel.

27. A non-transitory machine-readable medium for processing medical image data, comprising:
code operable for partitioning image data representative of a plurality of blood vessels into a plurality of sub-volumes that each include image data representative of the blood vessels, wherein the sub-volumes are defined by the physiological characteristics of the vessels within the respective sub-volumes
code operable for identifying a relative endpoint of a blood vessel of the plurality of blood vessels, wherein the blood vessel is identified based on the location of the relative endpoint;
code operable for labeling a first voxel with data to identify the first voxel as corresponding to the relative endpoint of the blood vessel;
code operable for tracking a path through image data representative of a plurality of blood vessels from the relative endpoint of the blood vessel toward a relative starting point of the blood vessel; and
code operable for labeling each voxel along the path as corresponding to the blood vessel.

28. A non-transitory machine-readable medium for processing medical image data, comprising:
code for partitioning image data representative of a plurality of blood vessels into a plurality of sub-volumes that each include image data representative of the blood vessels, wherein the sub-volumes are defined by the physiological characteristics of the vessels within the respective sub-volumes;
code for identifying a relative endpoint of a blood vessel within a sub-volume of the plurality of sub-volumes;
code for tracking a path through image data representative of a plurality of blood vessels from the relative endpoint of the blood vessel back toward a relative starting point of the blood vessel; and
code for labeling a bifurcation point when a first path tracked through the plurality of blood vessels merges with a second path tracked through the plurality of blood vessels.

29. A system for processing medical image data, comprising:
means for partitioning image data representative of a plurality of blood vessels into a plurality of sub-volumes, wherein each sub-volume includes image data representative of blood vessels and the sub-volumes are defined by the physiological characteristics of the vessels within the respective sub-volumes;
means for identifying a first voxel corresponding to a relative endpoint of a blood vessel;
means for identifying the blood vessel corresponding to the first voxel based on the sub-volume in which the first voxel is located; and
means for labeling the first voxel with data to identify the first voxel as being part of the blood vessel.

30. A system for processing medical image data, comprising:
means for partitioning image data representative of a plurality of blood vessels into a plurality of sub-volumes that each include image data representative of the blood vessels, wherein the sub-volumes are defined by the physiological characteristics of the vessels within the respective sub-volumes;
means for identifying a relative endpoint of a blood vessel of the plurality of blood vessels, wherein the blood vessel is identified based on the location of the relative endpoint;
means for labeling a first voxel with data to identify the first voxel as corresponding to the relative endpoint of the blood vessel;
means for tracking a path through image data representative of a plurality of blood vessels from the relative endpoint of the blood vessel toward a relative starting point of the blood vessel; and
means for labeling each voxel along the path as corresponding to the blood vessel.

31. A system for processing medical image data, comprising:
means for partitioning image data representative of a plurality of blood vessels into a plurality of sub-volumes that each include image data representative of the blood vessels, wherein the sub-volumes are defined by the physiological characteristics of the vessels within the respective sub-volumes;
means for identifying a relative endpoint of a blood vessel within a sub-volume of the plurality of sub-volumes;
means for tracking a path through image data representative of a plurality of blood vessels from the relative endpoint of the blood vessel back toward a relative starting point of the blood vessel; and
means for labeling a bifurcation point when a first path tracked through the plurality of blood vessels merges with a second path tracked through the plurality of blood vessels.

* * * * *